US007504118B2

(12) United States Patent
Miller et al.

(10) Patent No.: US 7,504,118 B2
(45) Date of Patent: Mar. 17, 2009

(54) DIETARY SUPPLEMENTS CONTAINING EXTRACTS OF CINNAMON AND METHODS OF USING SAME TO ENHANCE CREATINE TRANSPORT

(75) Inventors: Peter Miller, Broomfield, CO (US); Timothy Romero, Sarasota, FL (US)

(73) Assignee: FHG Corporation, Spring Hill, TN (US)

( * ) Notice: Subject to any disclaimer, the term of this patent is extended or adjusted under 35 U.S.C. 154(b) by 0 days.

(21) Appl. No.: 10/823,429

(22) Filed: Apr. 12, 2004

(65) Prior Publication Data

US 2004/0224035 A1 Nov. 11, 2004

(51) Int. Cl.
*A61K 36/05* (2006.01)
*A61K 31/195* (2006.01)
(52) U.S. Cl. .................. 424/739; 514/554; 514/565
(58) Field of Classification Search .................. None
See application file for complete search history.

(56) References Cited

U.S. PATENT DOCUMENTS

| | | | | |
|---|---|---|---|---|
| 5,900,435 | A | 5/1999 | Meglasson | 514/565 |
| 5,968,900 | A | 10/1999 | Greenhaff et al. | 514/3 |
| 6,051,236 | A * | 4/2000 | Portman | 424/725 |
| 6,136,339 | A | 10/2000 | Gardiner | 424/439 |
| 6,172,114 | B1 * | 1/2001 | McCabe | 514/565 |
| 6,200,569 | B1 | 3/2001 | Cheng | 424/195.1 |
| 6,903,136 | B2 * | 6/2005 | Miller et al. | 514/556 |
| 2001/0008641 | A1 * | 7/2001 | Krotzer | 424/725 |
| 2001/0022980 | A1 | 9/2001 | Bell et al. | 424/771 |
| 2003/0224062 | A1 | 12/2003 | Miller et al. | 424/646 |
| 2004/0028751 | A1 | 2/2004 | Mae et al. | 424/684 |
| 2005/0281896 | A1 * | 12/2005 | Gardiner et al. | 424/729 |
| 2006/0280814 | A1 * | 12/2006 | Gardiner et al. | 424/729 |
| 2008/0063689 | A1 * | 3/2008 | Farber | 424/439 |

OTHER PUBLICATIONS

Internet website http://www.dcdoctor.com/pages/rightpages_wellnesscenter/dietandnutrition/nutritionguide/nutriguide_weightloss.html. 3 pages.*
Internet website "Weight Loss Herbs" (2002), (3 pages total).*
A.L. Green, E. Hultman, I.A. MacDonald, D.A. Sewell and P.L. Greenhaff, "Carbohydrate ingestion augments skeletal muscle creatine accumulation during creatine supplementation in humans," 1996, American Journal of Physiology, 271(5): E821-E826.
R.A. Anderson, C.L. Broadhurst, M.M. Polansky, W.F. Schmidt, A. Khan, V.P. Flanagan, N.W. Schoene and D.J. Graves, "Isolation and Characterization of Polyphenol Type-A Polymers from Cinnamon with Insulin-like Biological Activity," 2004, Journal of Agricultural and Food Chemistry, 52: 65-70.
C.L. Broadhurst, M.M. Polansky and R.A. Anderson, "Insulin-like Biological Activity of Culinary and Medicinal Plant Aqueous Extracts in Vitro," 2000, J. Agric. Food Chem, 48(3): 849-852.
M.D. Althuis, N.E. Jordan, E.A. Ludington and J.T. Wittes, "Glucose and insulin responses to dietary chromium supplements: a meta-analysis," 2002, Am J. Clin Nutr, 76(1): 148-155.
G.R. Steenge, J. Lambourne, A. Casey, I.A. MacDonald and P.L. Greenhaff, "Stimulatory effect of insulin on creatine accumulation in human skeletal muscle," 1998, Am. J. Physiol. 275(38): E974-E979.
S.I. Kreydiyyeh, J. Usta and R. Copti, "Effect of cinnamon, clove and some of their constituents on the $Na^+$—$K^+$- ATPase activity and alanine absorption in the rat jejunum," 2000, Food and Chemical Toxicology 38(9): 755-762.
K.J. Jarvill-Taylor, Ph.D., R.A. Anderson, Ph.D., and D.J. Graves, Ph.D., "A Hydroxychalcone Derived from Cinnamon Functions as a Mimetic for Insulin in 3T3-L1 Adipocytes," 2001, Journal of the American College of Nutrition, 20(4): 327-336.
A. Khan, N.A. Bryden, M.M. Polansky and R.A. Anderson, "Insulin Potentiating Factor and Chromium Content of Selected Foods and Spices," 1990, Biological Trace Element Research, 24(3): 183-188.
J. McBride, "Cinnamon Extracts Boost Insulin Sensitivity," Jul. 2000, Agricultural Research, p. 21.
Y. Huang and S.H. Ho, "Toxicity and Antifeedant Activities of Cinnamaldehyde Against the Grain Storage Insects, *Tribolium castaneum* (Herbst) and *Sitophilus zeamais* Motsch," 1998, J. Stored Prod. Res., 34(1): 11-17.
S. Onderoglu, S. Sozer, K.M. Erbil, R. Ortac and F. Lermioglu, "The Evaluation of Long-term Effects of Cinnamon Bark and Olive Leaf on Toxicity Induced by Streptozotocin Administration to Rats," 1999, J. Pharm. Pharmacol, 51(11): 1305-1312.
N. Cheng, N. Cheng, X. Zhang, Y-D. I. Chen, B.J. Stoecker, and R.A. Anderson, "Hypoglycemic Effects of Cinnamon, Heshouwu & Mushroom Extracts in Type 2 Diabetes Mellitus," 2002, FASEB J., Experimental Biology 2002: Meeting Abstracts, 16: A647.
J. Imparl-Radosevich, S. Deas, M.M. Polansky, D.A. Baedke, T.S. Ingebritsen, R.A. Anderson and D.J. Graves, "Regulation of PTP-1 and Insulin Receptor Kinase by Fractions from Cinnamon: Implications for Cinnamon Regulation of Insulin Signalling," 1998, Horm Res, 50(3): 177-182.
J. Mancini-Filho, A. Van-Koiij, D.A.P. Mancini, F.F. Cozzolino and R.P. Torres, "Antioxidant activity of cinnamon (*Cinnamomum Zeylanicum*, Breyne) extracts," 1998, Bollettino Chimico Farmaceutico, 137(11): 443-447.
Green et al. "Carbohydrate ingestion augments creatine retention during creatine feeding in humans" Acta Physiol Scand (1996) 158, pp. 195-202.

* cited by examiner

*Primary Examiner*—Christopher R. Tate
(74) *Attorney, Agent, or Firm*—Gifford, Krass, Sprinkle, Anderson & Citkowski, P.C.

(57) ABSTRACT

Materials derived from cinnamon can be administered orally to humans or animals for the purpose of controlling blood glucose as well improving glucose tolerance. Controlling glucose metabolism is essential for those with impaired glucose metabolism as is the case for those with Type II diabetes where insulin function is not properly functioning. Such administration can also be used for the purpose of enhancing nutrient transport for purposes of athletic performance and controlling bodyweight and body fat levels. Similarly related, such administration can also be used for the purpose of enhancing creatine transport into excitable tissues such as skeletal muscle. The material can be administered as extracts of cinnamon and can be administered in a variety of ways including capsules, tablets, powdered beverages, bars, gels or drinks.

6 Claims, No Drawings

DIETARY SUPPLEMENTS CONTAINING EXTRACTS OF CINNAMON AND METHODS OF USING SAME TO ENHANCE CREATINE TRANSPORT

FIELD OF THE INVENTION

The present invention is directed to dietary supplements comprising cinnamon, or extracts thereof or derivatives of the extracts thereof, and to methods of using these dietary supplements to enhance nutrient transport and to promote weight loss, both in humans and animals.

BACKGROUND

Type II diabetes is quickly becoming an epidemic in the United States. The increased incidence of Type II diabetes has been attributed to diets characterized by high fat intake and repeated ingestion of refined foods and sugars, coupled with low fiber and vegetable intake. Diet, along with the natural aging process, causes a deterioration in the way in which the body metabolizes blood glucose. When the body cannot properly metabolize blood glucose, a tendency to store glucose as fat typically occurs. This is one reason levels of body fat increase with age. Diabetes is also known to be associated with a variety of other ailments including heart disease, hypertension, and obesity. There is a known link between insulin resistance and increased visceral adiposity. Diabetes is also a leading cause of glaucoma and other conditions related to a decrease in the quality of life.

It has long been known that natural and/or synthetic substances may aid in controlling blood glucose and enhancing nutrient transport. Such substances act by a variety of mechanisms. For example, some substances act by mimicking the effects of endogenous insulin and are therefore capable of replacing endogenous insulin. Such substances include synthetic insulin injections such as those which are routinely prescribed to individuals with Type I diabetes. Other commonly prescribed substances known to mimic the effects of insulin include the naturally occurring compounds taurine, 4-hydroxyisoleucine, arginine, and vanadium. Although these compounds have been shown to work as insulin mimetics by acting in the body to decrease serum blood glucose levels, they have not been successfully developed into viable treatments for disorders of glucose metabolism.

Still other substances act directly to increase what is termed insulin sensitivity or glucose tolerance. Glucose intolerance forces the body to generate additional insulin in an effort to lower blood glucose. This causes stress on the beta-cells of the pancreas and is thought to be a key contributor to Type II diabetes. In a state of glucose intolerance, the body mechanism for disposing of blood glucose is not functioning at its optimum level and therefore the system is inefficient. Substances which increase insulin sensitivity or glucose tolerance by assisting the body in returning to optimal levels of blood glucose include alpha-lipoic acid, pinitol and myo-inositol. These substances cannot entirely replace the function of endogenous insulin, but work at the receptor level alongside endogenous insulin to increase insulin sensitivity or glucose tolerance. Here, the action is exerted directly on the Glut-4 receptor of the cell to trigger the cascade normally caused by insulin that allows for the reduction in blood sugar via the transport of nutrients into the cell.

In the past, chromium was thought to aid in weight loss by controlling blood glucose and preventing the deposition of fatty acids. However, its actions were greatly limited and its claims never came to fruition. Cinnamon, known for its high concentration of chromium, has also been used for the control of blood glucose. However, researchers have demonstrated that cinnamon's effects are not from chromium, but rather from a different class of compounds. One study by Kahn et al. compared the chromium levels of foods and spices including cinnamon, and failed to find a correlation between chromium level and the level of insulin potentiation. (*Biological Trace Element Research*, 1990; 24:183-188). A meta-analysis by Althuis et al. showed no association between chromium and glucose or insulin concentrations. (*Am. J. Clin. Nutr.*, 2002; 76:148-55). A study by Broadhurst et al. has demonstrated that cinnamon is a strong potentiator of insulin in comparison to various other herbs and spices. (*J. Agric. Food Chem.*, 2000; 48:849-852).

One particular extract of cinnamon, methyl hydroxy chalcone polymer (MHCP), shows promising data in the area of glucose control. A recent study compared the effect of MHCP in 3T3-L1 adipocytes to that of insulin. (Jarvill-Taylor et al., *J. Am. College Nutr.*, 2001; 20:327-336). The results from that study support the theory that MHCP triggers the insulin cascade and subsequent transport of nutrients. The study also demonstrated that MHCP treatment stimulated glucose uptake and glycogen synthesis to a similar level as insulin. The study further demonstrated that treatment with endogenous insulin and MHCP resulted in a synergistic effect. Due to these conclusions it is suggested that MHCP may prove to be a very valuable tool in the fight against diabetes, where insulin is present.

In addition to benefiting Type II diabetics, cinnamon may benefit individuals with impaired glucose tolerance (i.e., pre-diabetics). Further, cinnamon has been shown to possess antioxidant activities related to lipid peroxidation. (Mancini-Filho et al., *Bollettino Chimico Farmaceutico*, 1998; 37:443-47). Cinnamon can be used as a food antioxidant and to enhance food palatability.

In broad terms, nutrient transport involves the deposit of nutrients into various tissues. For example, after the insulin cascade, the Glut-4 transport system triggered by insulin drives nutrients such as carbohydrates, amino acids (e.g., glutamine, arginine, leucine, taurine, isoleucine and valine) and creatine into skeletal tissue. Typically, water is driven into the cells at the same time.

Creatine is a natural dietary component primarily found in animal products. In the body, creatine is stored predominantly in skeletal muscle, and mostly in the form of phosphorylated creatine, but also in its free state. Total creatine content of mammalian skeletal muscle (i.e., creatine and phosphorylated creatine) typically varies from about 100 to about 140 mmol/kg. The level of creatine and phosphorylated creatine present in skeletal muscle can be increased through dietary supplementation with creatine.

The fuel for all muscular work in the body is adenosine tri-phosphate, or ATP. During intense exercise, ATP is utilized very rapidly. The body does not store much ATP in muscle so other substances must be broken down in order to replenish the ATP that is rapidly broken down during exercise. If the ATP is not replenished, fatigue occurs and force/power production declines. Of all the substances in the body that can replenish ATP, the fastest is phosphorylated creatine. Thus, the primary function of phosphorylated creatine in muscle is to buffer ATP by preventing decreases in ATP during exercise.

Creatine is taken up into tissues, such as skeletal muscle, by means of an active transport system that typical involves an insulin dependent pathway. In a study by Stengee et al., insulin was co-infused along with creatine supplementation. (*Am. J. Physiol.*, 1998; 275:E974-79). The results of this study indicated that insulin can enhance creatine accumulation in muscle, but only if insulin levels are present at extremely high or supra-physiological concentrations. Stengee et al. refers to a previous study by Green et al. which involved experimentation with ingestion of creatine in combination with a carbohydrate-containing solution to increase muscular uptake of creatine by creating physiologically high plasma insulin concentrations. Stengee et al. reports that Green et al. had found the quantity of carbohydrate necessary to produce a significant increase in creatine uptake, as compared to creatine supplementation alone, was close to the limit of palatability.

Thus, there exists a need in the art for a viable method of increasing the uptake of creatine into mammalian tissue, such as skeletal muscle. Further, there exists a need in the art for a dietary supplement whose administration at normal physiological concentrations would effect such an increase in creatine uptake.

SUMMARY

Disclosed herein is: (a) a dietary supplement comprising cinnamon, or an extract thereof or a derivative of the extract thereof and a nutrient, or a derivative or a precursor thereof, with or without a carbohydrate; and (b) methods of increasing the uptake of nutrients in mammalian muscle, enhancing nutrient transport, and enhancing athletic performance comprising administration of said dietary supplement.

Accordingly, it is an object of the invention to provide a method and a dietary supplement which will enhance the uptake of nutrients into mammalian muscle. More specifically, it is an object of the invention to provide a method and a dietary supplement which will enhance the uptake of creatine into skeletal muscle. It is a further object of the invention to provide a method and a dietary supplement that triggers an insulin dependent pathway to enhance the uptake of creatine into skeletal muscle. It is a still further object of the invention to provide a method and a dietary supplement that achieves these objects when administered in physiologically acceptable amounts.

Also disclosed herein is: (a) a dietary supplement comprising cinnamon, or an extract thereof or a derivative of the extract thereof and (b) methods of losing weight and reducing body fat comprising administration of said dietary supplement.

Accordingly, it is also an object of the invention to provide a method and a dietary supplement which will promote weight loss and body fat reduction.

Other objectives, advantages and features of the invention will become apparent from the following detailed description, and from the claims.

BRIEF DESCRIPTION OF THE PREFERRED EMBODIMENT

The creatine-containing dietary supplements of the invention comprise cinnamon, or an extract thereof or a derivative of the extract thereof and creatine, or a derivative or a precursor thereof, with or without a carbohydrate.

Additionally, the body fat reduction and weight loss dietary supplements of the invention comprise cinnamon, or an extract thereof or a derivative of the extract thereof.

Cinnamon is one of the world's most popular spices. Cinnamon contains over one hundred different chalcones within it. Chalcones are a type of polyphenol or flavonoid. These chalcones may be extracted from cinnamon and isolated, and, optionally, derivatized. One chalcone which can be extracted from cinnamon is the phytochemical methyl hydroxy chalcone polymer, or MHCP. In a preferred embodiment of the invention, the dietary supplement includes MHCP.

The isolation of phytochemicals from cinnamon follows the general process of aqueous extraction followed by centrifugation to remove non-soluble compounds. Specifically, MHCP and other water-soluble polyphenol polymers can be extracted from cinnamon using the following process: 5 g cinnamon and 100 ml 0.1 N acetic acid are combined and autoclaved for 15 minutes. The resultant mixture is cooled, then centrifuged and the precipitate discarded. Four volumes of ethanol/0.1 N acetic acid are added to the supernatant and the mixture is stored overnight at 4 C°. The mixture is screened through a filter and then introduced onto an LH-20 column and washed with 600 ml ethanol/0.1 N acetic acid. The desired fraction is then eluted with a 1:1 mixture of acetonitrile and 0.2 N acetic acid. The eluent is then concentrated and introduced onto a HPLC column at 275 nm.

The chemical name for creatine is methylguanidino acetic acid. This is the free form of creatine. Known creatine derivatives include creatine monohydrate and other hydrates, creatine salts such as creatine citrate, creatine esters, phosphorylated creatine, and creatine pyruvate. Known creatine precursors include glycocyamine or Guanidineacetic Acid and the amino acids arginine, glycine, and methionine. In a preferred embodiment of the invention for the creatine-containing dietary supplements, the dietary supplement includes creatine monohydrate.

The optional carbohydrate in the creatine-containing dietary supplements of the invention include simple sugars such as the monosaccharides glucose and dextrose.

Typical formulations of creatine-containing dietary supplements according to the invention include: dietary supplements containing from about 0.1 mg to about 100 mg of cinnamon extract or cinnamon extract derivative per gram of dietary supplement; dietary supplements containing from about 1 mg to about 900 mg of creatine or creatine derivative or creatine precursor per gram of dietary supplement, and preferably from about 50 mg to about 125 mg of creatine or creatine derivative or creatine precursor per gram of dietary supplement; dietary supplements containing from about 1 mg to about 950 mg of carbohydrate per gram of dietary supplement, preferably from about 400 mg to about 900 mg of carbohydrate per gram of dietary supplement, and more preferably from about 500 mg to about 800 mg of carbohydrate per gram of dietary supplement.

Typical formulations of the body fat reduction and weight loss dietary supplements of the invention include dietary supplements containing from about 1 mg to about 1,000 mg of cinnamon extract or cinnamon extract derivative per gram of dietary supplement.

Typical daily dosages of the creatine-containing dietary supplements of the invention are about 10 mg to about 10,000 mg of cinnamon extract or cinnamon extract derivative and about 100 mg to about 25,000 mg of creatine or creatine derivative or creatine precursor, and preferably about 500 mg to about 10,000 mg of creatine or creatine derivative or creatine precursor. Generally, the creatine-containing dietary supplements of the invention are administered in an amount of from about 200 mg to about 500 g per day.

Typical daily dosages of the body fat reduction and weight loss dietary supplements of the invention are about 10 mg to about 10,000 mg of cinnamon extract or cinnamon extract derivative. Generally, the body fat reduction and weight loss dietary supplements of the invention are administered in an amount of from about 100 mg to about 500 g per day.

The dietary supplements of the invention are orally administered and can be in the form of capsules, tablets, powdered beverages, bars, gels or drinks.

Administration of the dietary supplements of the invention will mimic the effects of insulin and will decrease glucose intolerance, thereby increasing the efficiency of insulin. As a result, administration of the creatine-containing dietary supplements of the invention will enhance the transport of creatine into tissues such as skeletal muscle. The increase in the amount of creatine storage in the muscle can be measured by muscle biopsy. Upon administration of the creatine-containing dietary supplements of the invention for a period of days (e.g., for as little as 4 days and as many as 30 days), the total creatine content of skeletal muscle (i.e., free and phosphorylated creatine) will increase from about 10% to about 40% where typical levels of total creatine in skeletal muscle prior to administration are between about 100 to about 140 mmol/kg of dry muscle.

Administration of the body fat reduction and weight loss dietary supplements of the invention, particularly to individuals with impaired glucose tolerance, will have the effect of restoring optimal glucose functioning, therefore lessening the likelihood of adipose storage, and leading to a reduction in body fat and weight.

EXAMPLE 1

Four subjects (males ages 18-45 yr) consumed one serving of a dietary supplement as described herein four times per day for five days. Each serving of the dietary supplement is approximately 96 g and includes the following active ingredients:

| Compound | Amount |
| --- | --- |
| creatine monohydrate | about 7.5 g |
| creatine magnesium chelate | about 2.5 g |
| Cinnulin PF ® (a source of water-soluble extracts of cinnamon available from Integrity Nutraceuticals International) | about 200 mg |
| carbohydrates (dextrose, maltodextrin, trehalose and maltose) | about 69 g |

Each approximate 96 g serving is mixed with 8 ounces of water to provide a liquid drink for consumption. The subjects followed a weight-lifting regime on four out of the five days. On these four workout days, the subjects consumed one serving of the dietary supplement 60 minutes before working out and another serving of the dietary supplement immediately after finishing working out. The subjects consumed the remaining two servings of the dietary supplement with carbohydrate-containing meals. On the one non-workout day, the subjects consumed one serving of the dietary supplement every four hours. This study demonstrated that administration of the dietary supplement caused an average 20% increase in strength among the subjects, as measured by benchpress (number of repetitions) to failure.

The examples and embodiments set forth in the present application are provided only to illustrate various aspects of the invention and additional embodiments and advantages of the dietary supplements and methods of the present invention will be apparent to those skilled in the art.

What is claimed is:

1. A dietary supplement consisting essentially of:
   a. a first ingredient consisting of: a water-soluble extract of cinnamon;
   b. a second ingredient consisting essentially: of creatine monohydrate, and/or a creatine magnesium chelate; and
   c. optionally, at least one carbohydrate;
   wherein said water-soluble extract of cinnamon functions synergistically with said second ingredient at a daily intake of between 10 and 2,000 milligrams of said water-soluble extract of cinnamon and between 100 and 25,000 milligrams of said second ingredient to increase the uptake of creatine by a muscle of a subject by an insulin dependent pathway and said water-soluble extract of cinnamon decreases glucose intolerance.

2. The dietary supplement of claim 1, wherein the carbohydrate is selected from the group consisting of dextrose, maltose, maltodextrin and trehalose.

3. The dietary supplement of claim 1 wherein element (a) is present in an amount from about 0.1 mg to about 100 mg per gram of dietary supplement and element (b) is present in an amount from about 10 mg to about 900 mg per gram of dietary supplement and the dietary supplement lacks said at least one carbohydrate.

4. The dietary supplement of claim 3 wherein said at least one carbohydrate is present in an amount of from about 1 mg to about 950 mg per gram of dietary supplement.

5. The dietary supplement of claim 1, wherein said water-soluble extract of cinnamon is further characterized in that it is comprised of a fraction of cinnamon which is soluble in 0.1 N acetic acid.

6. The dietary supplement of claim 1, wherein element (a) is present in the amount of 2 mg per gram of the dietary supplement and element (b) is present in an amount of 104 mg per gram of the dietary supplement and the at least one carbohydrate is present.

* * * * *

UNITED STATES PATENT AND TRADEMARK OFFICE
CERTIFICATE OF CORRECTION

| | | |
|---|---|---|
| PATENT NO. | : 7,504,118 B2 | |
| APPLICATION NO. | : 10/823429 | |
| DATED | : March 17, 2009 | |
| INVENTOR(S) | : Peter Miller et al. | |

It is certified that error appears in the above-identified patent and that said Letters Patent is hereby corrected as shown below:

On the title page, item [60] please add the following priority information:

--Related U.S. Application Data

Provisional application No. 60/462,100, filed on Nov. 4, 2003.--

Signed and Sealed this

Eleventh Day of August, 2009

David J. Kappos
*Director of the United States Patent and Trademark Office*